(12) United States Patent
Liang et al.

(10) Patent No.: US 6,598,975 B2
(45) Date of Patent: *Jul. 29, 2003

(54) APPARATUS AND METHOD FOR MEASURING VISION DEFECTS OF A HUMAN EYE

(75) Inventors: Junzhong Liang, Fremont, CA (US); James H. Burkhalter, Orlando, FL (US)

(73) Assignee: Alcon, Inc., Hunenberg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/919,374

(22) Filed: Jul. 31, 2001

(65) Prior Publication Data

US 2003/0020872 A1 Jan. 30, 2003

(Under 37 CFR 1.47)

Related U.S. Application Data

(63) Continuation-in-part of application No. 09/665,748, filed on Sep. 20, 2000, now Pat. No. 6,270,221, which is a continuation of application No. 09/274,672, filed on Mar. 24, 1999, now abandoned.
(60) Provisional application No. 60/097,086, filed on Aug. 19, 1998.

(51) Int. Cl.[7] ................................................. A61B 3/10
(52) U.S. Cl. ..................................................... 351/221
(58) Field of Search ................................. 351/205, 211, 351/213, 214, 215, 221, 246, 212, 219, 247; 607/88, 89

(56) References Cited

U.S. PATENT DOCUMENTS 6,095,651 A * 8/2000 Williams et al. ............. 351/246
6,155,684 A * 12/2000 Bille et al. ................... 351/212
6,270,221 B1 * 8/2001 Liang et al. .................. 351/221

* cited by examiner

Primary Examiner—Marvin M. Lateef
Assistant Examiner—John R Sanders
(74) Attorney, Agent, or Firm—Allen, Dyer, Doppelt, Milbrath & Gilchrist, P.A.

(57) ABSTRACT

Optical characteristics, including vision defects, of optical systems, such as the eye, are measured using a collimated beam from a diode laser focused at a position relative to the eye other than the retina for providing a finite source of secondary radiation on the retina of the eye, the image of which is close to a desired diffraction-limited spot. The secondary radiation is reflected back from the retina as a reflected wavefront of radiation that passes through the eye and is directed onto a wavefront analyzer where distortions associated with the reflected wavefront are measured. By focusing on the cornea through a long-focal-length lens and thus converging the beam through a small angle, as opposed to focusing a collimated light onto the retina, the need for lenses or lens combinations and the time required to adjust such to accommodate the different visual characteristics of each patient is eliminated.

36 Claims, 4 Drawing Sheets

APPARATUS AND METHOD FOR MEASURING VISION DEFECTS OF A HUMAN EYE

CROSS-REFERENCE TO RELATED APPLICATIONS

This application is a continuation-in-part of application Ser. No. 09/665,748, filed Sep. 20, 2000, now U.S. Pat. No. 6,270,221, which is a continuation of application Ser. No. 09/274,672, filed Mar. 24, 1999, now abandoned, which claimed priority to U.S. Provisional Application having Serial No. 60/097,086, filed on Aug. 19, 1998, for "Apparatus and Method for Measuring Vision Defects of a Human Eye," commonly owned with the instant application.

BACKGROUND OF INVENTION

1. Field of Invention

The invention relates generally to optical aberration measurement and correction, and in particular to projection techniques in the objective measurement and correction of the human eye using a wavefront sensor.

2. Description of Background Art

There has been and continues to be a need to provide a person with improved visual acuity. Remodeling of the cornea using refractive laser surgery or intracorneal implants, adding synthetic lenses using intraocular lens implants or precision ground contact lenses or eye glasses provide known solutions. Further, it is known to correct vision astigmatically by surgical modification of myopic or hyperopic astigmatism through laser keratoplasty, keratomileusis, or photorefractive keratectomy. Laser sources are used to erode or ablate surfaces of the eye, typically reshaping the cornea. Prior to and during such surgery, precise measurements must be made to determine required surgical corrections.

The imprecise measurement technique of placing lenses of known refractive power anterior to the cornea and asking a patient which lens or lens combination provides the clearest vision has been improved with the use of autorefractometers, as described in U.S. Pat. No. 5,258,791 to Penny et al., or with the use of wavefront sensors as described by Liang et al. in "Objective Measurement of Wave Aberrations of the Human Eye with the Use of a Hartmann-Shack Wave-Front Sensor," Journal of the Optical Society of America, Vol. 1, No. 7, July 1994, pp. 1949–1957, byway of example. Penny '791 discloses the use of autorefractometer measurements for determining the appropriate corneal surface reshaping to provide emmetropia, a condition of a normal eye when parallel rays are focused exactly on the retina and vision is optimum. Spatially resolved refraction data, in combination with measured existing surface contour of the anterior surface of the eye, enable a calculation of a detailed spatially resolved new contour that provides corrected vision.

It would be an improvement in the art if such vision correction could be made without the need for these contour data, and further without the need for feedback from the patient regarding an appropriate lens. Liang et al. disclose the use of a Hartmann-Shack wavefront sensor to measure ocular aberrations by measuring the wavefront emerging from the eye by retinal reflection of a focused laser light spot on the retina's fovea. A parallel beam of laser light passes through beam splitters and a lens pair that brings the beam to a focus point on the retina by the optics of the eye. Possible myopia or hyperopia of the tested eye is corrected by movement of a lens within the lens pair. The focused light on the fovea is then assumed to be diffusely reflected and acts as a point source located on the retina. The reflected light passes through the eye and forms a distorted wavefront in front of the eye that results from the ocular aberrations. The aberrated wavefront is then directed to the wavefront sensor.

A point source of radiation on the retina would be ideal for such measurements. However, when the perfect eye receives a collimated beam of light, the best possible image on the retina is a diffraction-limited spot. As illustrated by way of example, with Penny et al. and Liang et al., discussed above, and typical for those of skill in the art, parallel or collimated beams are used with the optics of the eye being measured to achieve this diffraction-limited spot for such objective measurements. To do so requires that a setup for each patient include a corrective lens or lens combination and adjustments thereto for accommodating that patient's specific visual acuity. Providing a corrective or lens combination, as well as setting up for its use, becomes cumbersome and time consuming, and requires additional expense. Eliminating the need for such corrective optics is desirable and eliminates a variable within optical measurement systems that typically include many variables. Further, there is a need for providing optical characteristics of an eye without requiring feedback from the patient. By way of example, the patient may be a wild or domestic animal, living or dead.

SUMMARY OF INVENTION

In view of the foregoing background, it is therefore an object of the present invention to provide a refraction measurement system that easily accommodates the measurement of vision characteristics of the eye, even in the presence of finite refractive errors.

It is another object to improve upon the time required for a patient to be in a fixed position during examination, while at the same time providing a useful source of light on the retina of the eye to be measured regardless of the characteristics of the eye of that patient or other patients to be examined.

It is a further object to measure such characteristics without requiring patient or operator feedback.

These and other objects, advantages and features of the present invention, are provided by a method aspect of the invention for measuring optical characteristics of an optical system including the focusing of an optical beam proximate an anterior surface of the optical system, for placing a finite source of secondary radiation on a focal surface of the optical system, which secondary radiation is emitted from the focal surface as a reflected wavefront of radiation that passes through the optical system, projecting the reflected wavefront onto a wavefront analyzer, and measuring characteristics of the optical system associated with the reflected wavefront.

In a preferred embodiment, the method includes the step of measuring defects of the eye, which includes the steps of focusing an optical beam onto an anterior surface of the eye, other than the retina, for providing a finite source of secondary radiation on the retina of the eye, which secondary radiation is emitted from the retina as a reflected wavefront of radiation that passes through the eye, directing the reflected wavefront onto a wavefront analyzer, and measuring distortions associated with the reflected wavefront. A preferred embodiment of the invention includes the step of focusing the projected optical beam on the anterior surface of the cornea. In an alternate embodiment the optical beam is focused behind the retina.

An apparatus for effectively performing such measurements includes means for focusing an optical beam onto an anterior surface of the optical system or eye, other than the retina, for providing a finite secondary radiation source on the focal surface, or retina of the eye, which finite secondary radiation source is emitted from the retina as a reflected wavefront of radiation that passes through the eye, means for directing the reflected wavefront onto a wavefront analyzer, and a wavefront analyzer for measuring distortions associated with the reflected wavefront. In one preferred embodiment of the present invention, a laser beam is focused onto the surface of the cornea with a long-focal-length lens, which converges the beam through a small angle for passing through the iris of the eye and providing a finite secondary radiation source on the retina of the eye, which finite secondary radiation source is emitted from the retina through the optics of the eye as the wavefront to be measured. In an alternate embodiment the apparatus comprises means for focusing the optical beam behind the retina

BRIEF DESCRIPTION OF DRAWINGS

A preferred embodiment of the invention as well as alternate embodiments are described by way of example with reference to the accompanying drawings.

DETAILED DESCRIPTION OF PREFERRED EMBODIMENTS

The present invention will be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 1:
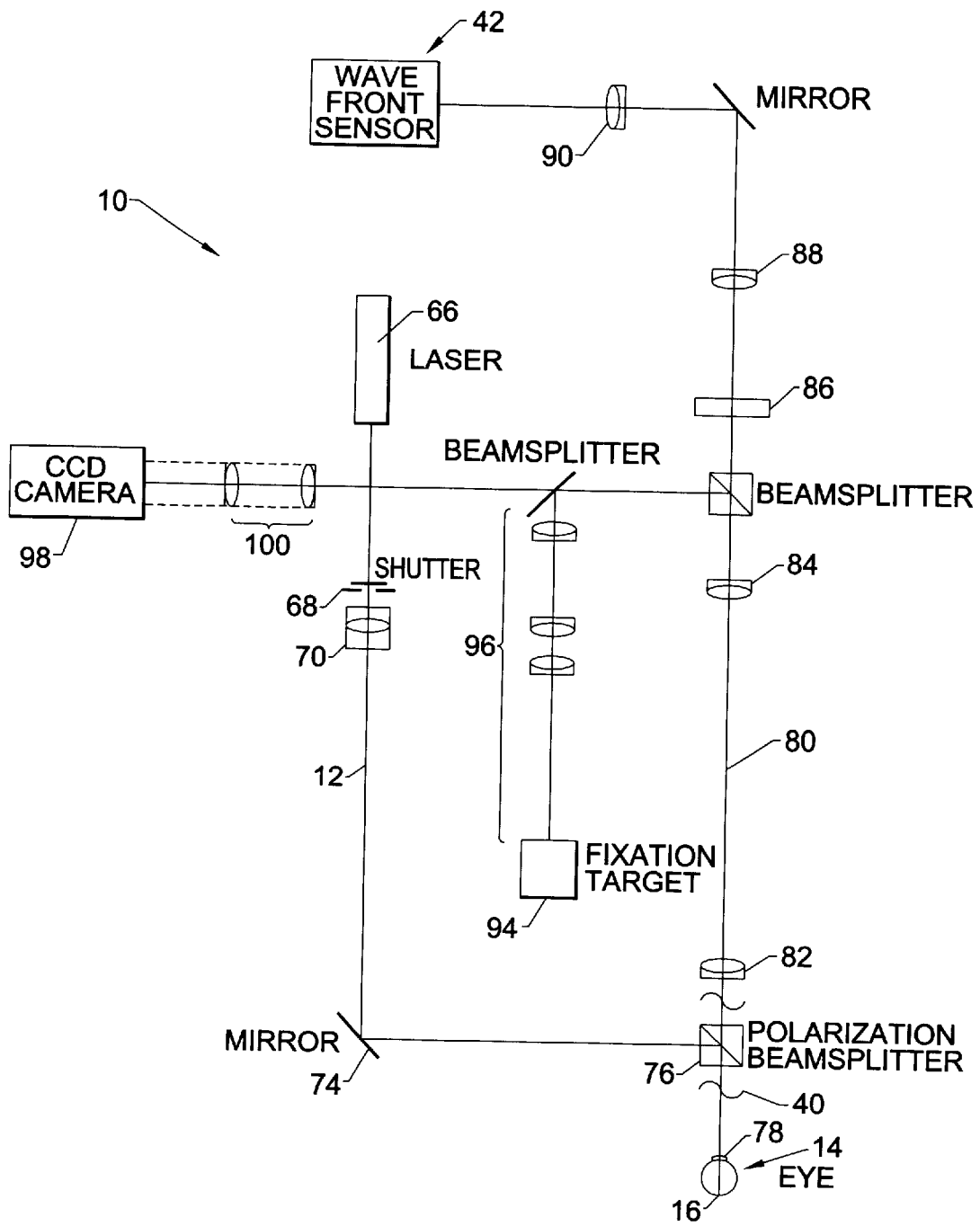
FIG. 1 is a diagrammatic illustration of an apparatus for measuring visual defects of an eye, according to the present invention.
Figure 2:
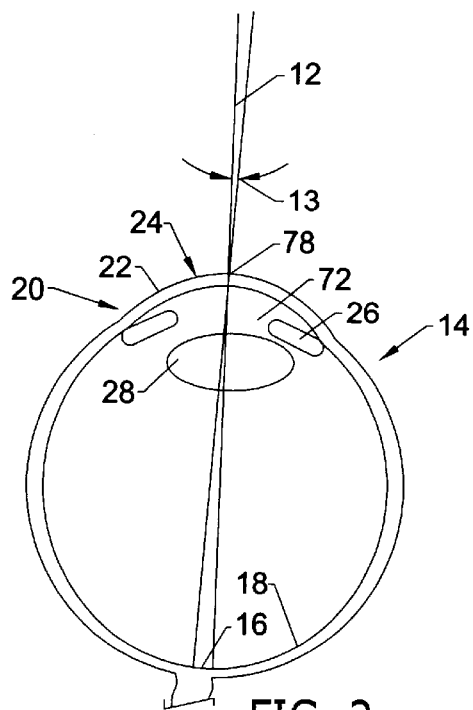
FIG. 2 is a diagrammatic illustration of an eye being measured by the apparatus of the present invention, with the focus on the cornea.

A preferred embodiment of a measurement apparatus 10 of the present invention is herein initially described with reference to the schematic diagram of FIG. 1. A projected beam 12 of optical radiation is directed into an eye 14 to be measured, so that a small area or measurable spot 16 is formed as a secondary radiation source in the foveal region of the retina 18 (FIG. 2). Specifically, the beam 12 is focused through a small angle 13 onto an anterior surface 20 of the eye 14, other than the retina, and in a preferred embodiment of the present invention, focused on an anterior corneal surface 22 of the cornea 24 for further projection through the iris 26 and lens 28 and onto the retina 18.

Figure 2A:
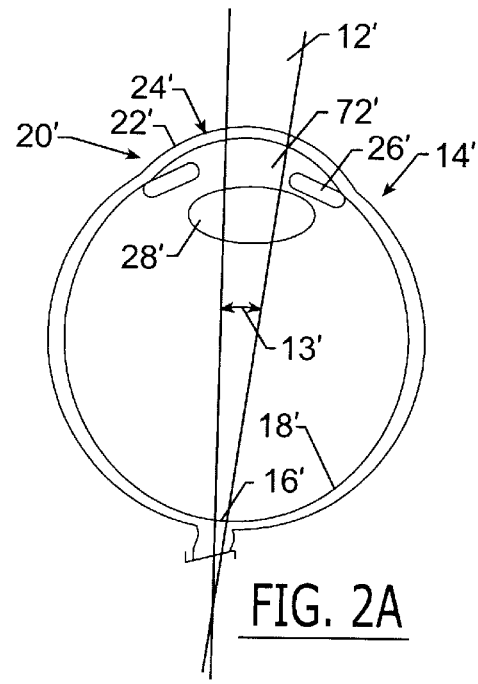
FIG. 2A is a diagrammatic illustration of an eye being measured by the apparatus of the present invention, with the focus behind the retina.

In an alternate embodiment of the invention, a projected beam 12' of optical radiation is directed into an eye 14' to be measured, so that a small area or measurable spot 16' is formed as a secondary radiation source in the foveal region of the retina 18' (FIG. 2A). Specifically, the beam 12' is focused through a small angle 13' at a point behind the eye 14', after passing through the iris 26', the lens 28', and the retina 18'.

Figure 3A:
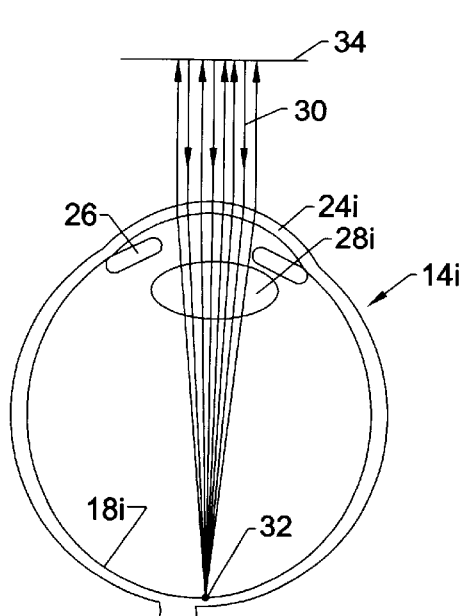
FIGS. 3A and 3B are diagrammatic illustrations of an ideal eye with perfect vision and an aberrated ideal eye, respectively.

By way of further background, consider an "ideal" eye 14$i$ with ideal vision, as illustrated with reference to FIG. 3A. The ideal eye 14$i$, having the ideal cornea 24$i$ and ideal lens 28$i$, will focus a collimated beam of light, illustrated with arrows 30 to a point 32, as the secondary radiation source, on the ideal retina 18$i$. This point 32 would then be a point source of light that would be diffusely reflected back through the optics of the ideal eye 14$i$ as a sequence of plane waves 34. In actual fact, even an eye having perfect vision, as illustrated by way of example with reference to FIG. 4, will produce a diffraction-limited illuminated area or spot 36 as the secondary radiation source on the retina of the eye, under the best possible circumstances. In a typical eye, as illustrated with reference to FIG. 4, such a spot 36 is even larger, where most of the blurring will be due to finite aberrations found in typical eyes. By way of further example, in an aberrated eye 14$a$, if the point source 32 could be realized, distorted wavefronts 38 result, as illustrated with reference to FIG. 3B. Having to deal with a series of distorted wavefronts 38 resulting from aberrations, and further dealing with a blurring of such distorted wavefronts 38 resulting from diffraction effects and the finite aberrations of the eye, results in a spot 36 source of light rather than a point 32 source, representing one of the challenges in measuring the visual defects or an eye.

Figure 4:
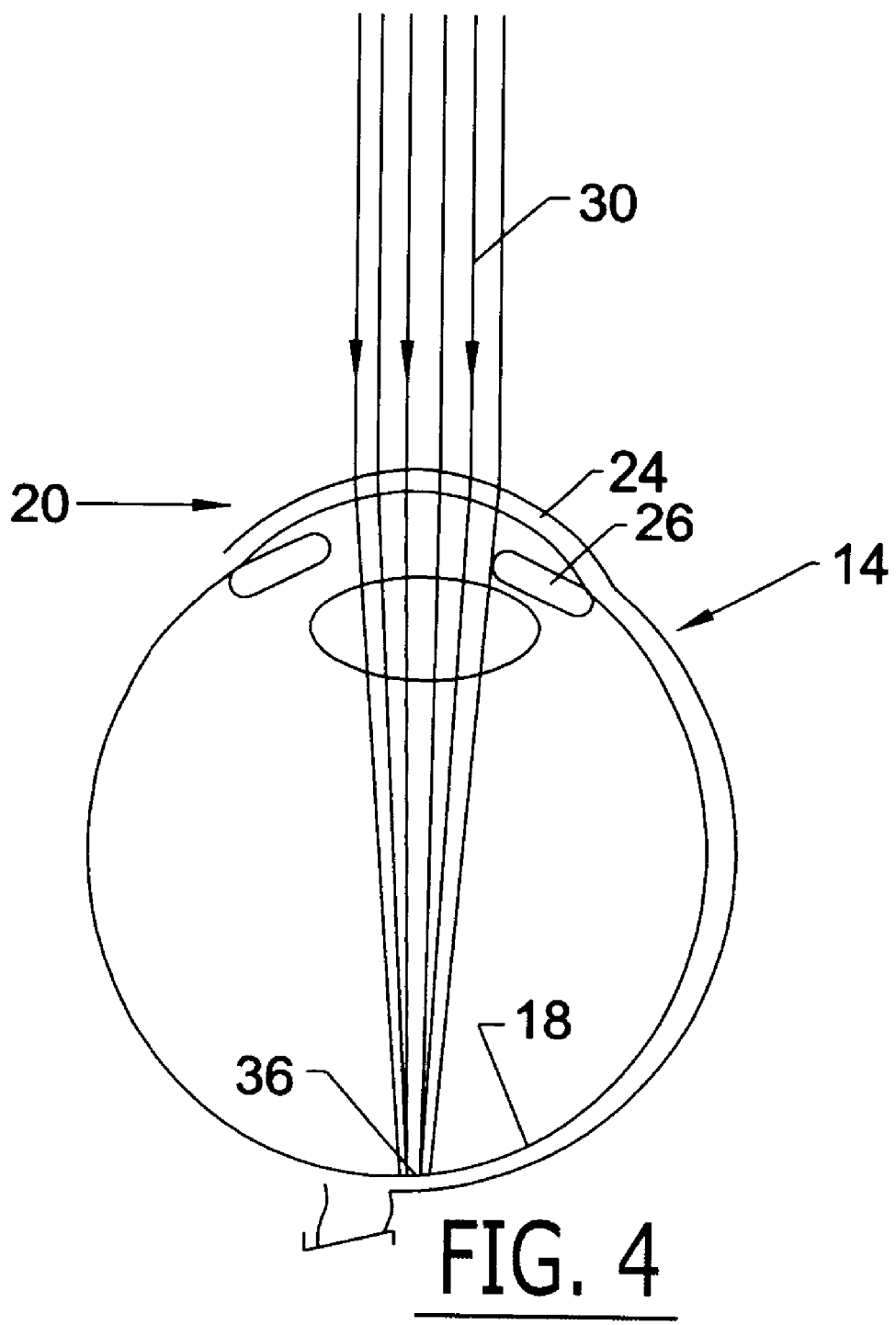
FIG. 4 is a diagrammatic illustration of an eye being measured with collimated light focused on the retina to a diffraction-limited spot.

It is typical in the art of eye measurement to form a collimated beam and attempt to focus the collimated beam onto the retina, using lenses and lens combinations with the optics of the eye to produce the smallest possible spot 36, as earlier described with reference to FIG. 4. Using lenses and focusing techniques typically takes valuable time and includes multiple attempts to focus a spot on the retina with the use of various lenses and lens combinations to accommodate the unique vision of each patient being measured. With the present invention, and the understanding that most of the blurring results from the curvature of the cornea, the present invention eliminates the need to find lenses or lens combinations to minimize the size of the spot on the retina that is used as the secondary source of radiation.

Figure 5:
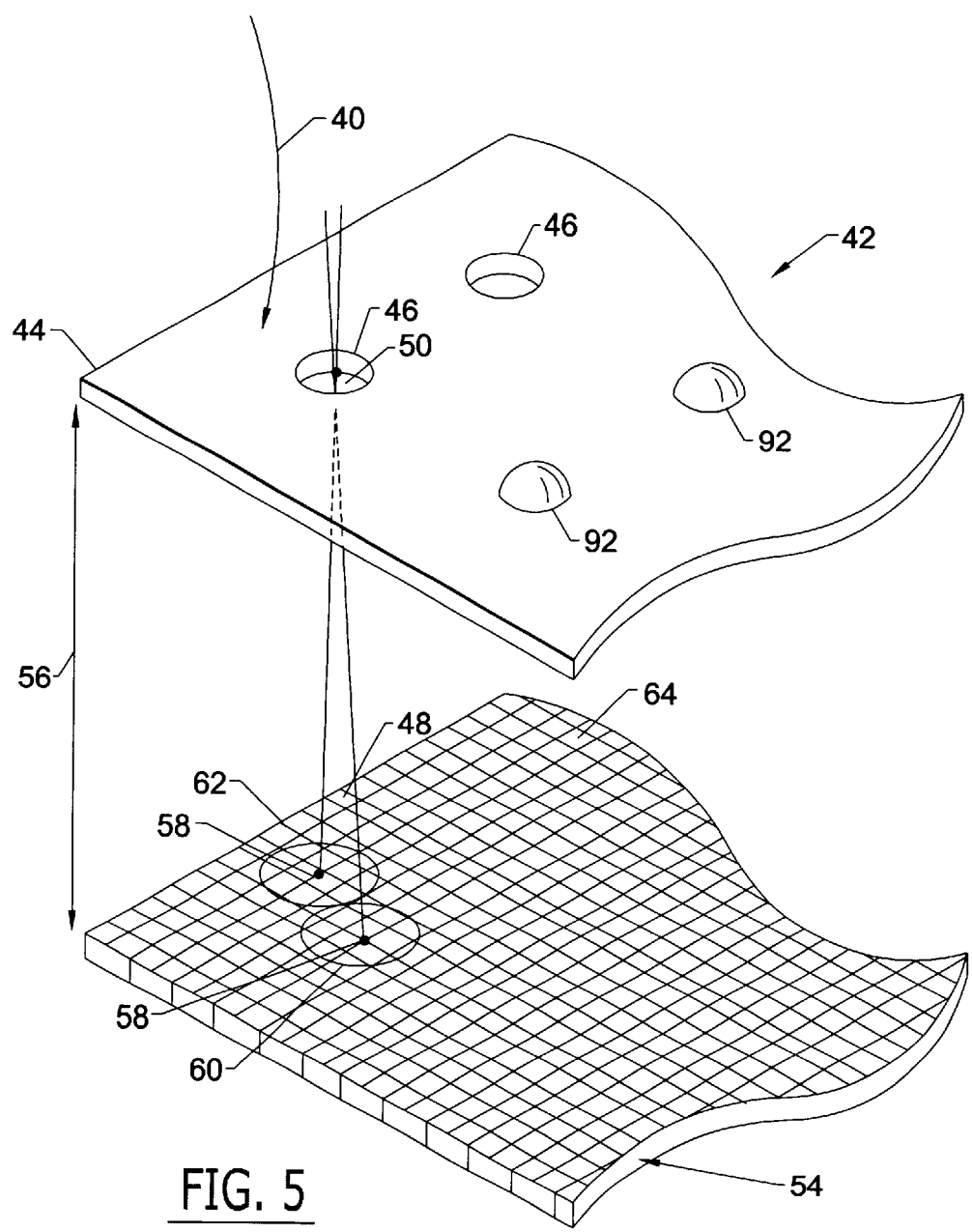
FIG. 5 is a partial perspective view of a pinhole imaging plate and detector plane of a wavefront sensor used in a preferred embodiment of the present invention.

With reference again to the embodiment described in FIGS. 1 and 2, the optical wavefronts 40 scattered from the retina 18 are transferred by a series of optical elements, which will be described in further detail in the following, to a wavefront sensor 42, which divides each incident wavefront into a group of "wavelets," referred to herein with numeral 50, using an opaque plate 44 having a planar array of apertures 46 (FIG. 5). Further, the wavefront sensor 42 records the position 48 at which each wavelet 50 passing through the aperture 46 strikes a detector plane 54 such as a charged-coupled device (CCD), herein provided as one preferred embodiment, the plane being held a fixed small distance 56 behind the plate 44. The transverse displacement 58 of each wavelet 50 at the CCD detector plane 54 from a collimated light reference position 60 is then used to calculate a wavefront slope at each position of the apertures 46 within the planar aperture array. Alternate methods exist for using partial derivative data resulting from the measurements of the slope to calculate the wavefront 40. One acceptable approach is that used by Liang et al. in the aforementioned paper, where the wavefront is closely approximated using Zernike polynomials.

At each position 48, a spot 62 typically extending beyond the light measurement area of one CCD element 64 is produced. As earlier discussed, blurring and a large diffraction-limited spot make it difficult to make measurements. Thus reducing blurring improves measurement at the detector plane 54.

With reference again to FIG. 1, in one preferred embodiment of the present invention, the apparatus 10 includes the projected beam 12 of linearly polarized light (S-component) emitted from a diode laser 66 (670 nm, 3 mW, by way of example). The beam of light passes through an electromechanical shutter 68, which controls the duration of light exposure on the eye 14 of the patient. The exposure of the retina 18 of the eye 14 illustrated with reference again to FIG. 2. It is expected that alternate sources of light, for example, noncoherent and nonpolarized as well as alternate light-transmitting techniques, will be recognized by those skilled in the art without deviating from the teachings of the present invention. As herein described, the use of coherent light from a laser and polarization techniques are currently preferred.

When the shutter 68 is open, the projected beam 12, collimated light from the diode laser 66, is directed by a long focal length lens 70 for focusing on the anterior surface 22 of the cornea 24 of the eye 14 (FIG. 2), passing through the pupil 72 and lens 28 of the eye 14, and onto the retina 18 as the small measurable spot 16. In an alternate embodiment, lens 70 comprises a zoom lens for varying the focus and moving the focus location as desired. By focusing on the cornea 24, the measurement is minimally dependent on the curvature of the cornea. However, other locations proximate the corneal surface are acceptable.

While diffraction and various aberrations are present, the present invention avoids the aberration effects from the cornea, which typically dominate. The lens 28 of the eye 14 contributes a relatively small aberration effect when compared with that of the cornea 24. Further, and with regard to the selection of lens 70, selecting a lens with a short focal length would provide a large angle 13, a well-focused point 78 on the surface of the cornea 24, and fewer aberration effects from the cornea. However, a large angle 13 results in an undesirably larger retinal spot 16. The small angle 13 herein described provides a larger focus point 78 on the cornea 24 but the more desirable smaller spot 16 on the retina 18. The spot 16 will depend on the wavelength, starting point size, and focal length of the lens 70 selected. In preferred embodiments of the present invention, lenses of approximate one-half meter are selected for the lens 70. A 100-mm lens 70 has also been effectively used.

In one preferred embodiment herein described, a mirror 74 and polarization beamsplitter 76 direct the projected beam 12 to a focus 78 on the anterior surface 20 of the cornea 24. The projected beam 12, focused on the anterior surface 22 of the cornea 24, provides the measurable spot 16 as a light source (about 1.5 milliradians in visual space, by way of example) on the retina 18 of the eye 14 being measured (FIG. 2). Such a spot 16 provides an acceptable substitute for a diffraction limited spot typically sought.

Figure 3B:
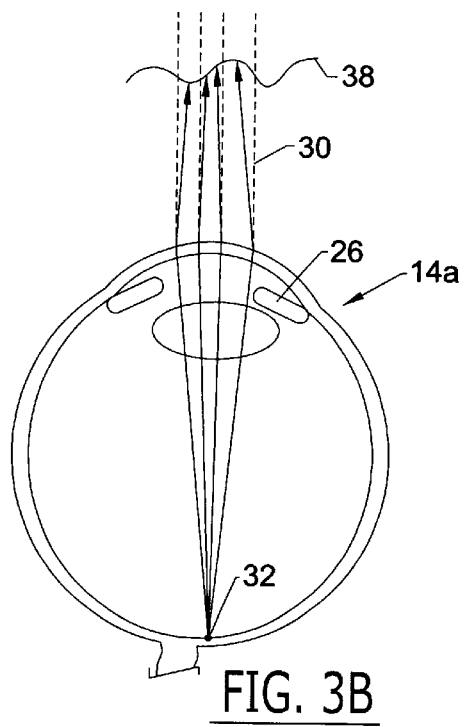

By way of one preferred example of use, a method for measuring vision characteristics of the eye 14 includes directing the beam 12 through the long-focal-length lens 70 for providing the small angle 13 (FIG. 2), about an optical path for passing the beam 12 through the pupil 72 of the eye 14. The beam 12 is first focused at a fixed location 78, without the eye or patient in place. All measuring equipment, the apparatus 10, is arranged without the patient in place and at a convenient time prior to measuring. Then the patient is positioned such that the anterior surface of the eye 14 of a patient is located at the fixed location 78, which in a preferred embodiment is the anterior surface of the cornea. This places a finite source of secondary radiation, the spot 16, as herein described, on the retina 18 of the eye 14, which provides light emitted from the retina 18 and through the pupil 72 as a reflected wavefront, the wavefront 38 (FIG. 3B). This wavefront 38 is directed onto the wavefront analyzer 42 for measurement.

In a preferred embodiment, the laser power reaching the eye is physically limited to a maximum of 7 $\mu$W. In measurements on a human eye using the apparatus 10, a laser pulse duration of 700 ms was used so that the total energy entering the eye would not exceed 4.9 $\mu$J. For comparison, according to the ANSI standard for direct "intrabeam" viewing, the maximum permissible exposure to a laser at the wavelength used is 530 $\mu$J. Thus the probing laser energies effectively used in the present invention are two orders of magnitude below an "eye-safe" limit.

With reference again to FIG. 2, the light diffusely reflected by the retina 18 produces the wavefront 40, a distorted wavefront at the pupil plane due to the eye's aberrations. Diffuse reflection makes the returning light from the retina depolarized, containing not only an S-component but also a P-component polarized light. The polarization beamsplitter 76 in front of the eye 14 will only let the P-component pass through it and downstream of the wavefront sensor 42. The S-component is essentially totally reflected toward the diode laser 66. Because the light reflected by corneal surface preserves the polarization of the incoming beam (S-polarized), the corneal reflection is reflected by the beamsplitter 76 and is thus rejected from the path 80 heading toward the wavefront sensor 42. The P-component of the aberrated wavefront 40 at the subject's pupil plane is then re-created by the combination of lens 82 and lens 84, at a trial lens plane 86 (FIG. 1). In one preferred embodiment, the diameter and the aperture of the lens 82 and lens 84 are 40 and 120 mm, respectively. The combination of lens 82 and lens 84 form an afocal image system with the eye's pupil 72 (the object plane) at the focal plane of the lens 82, and the image plane, trial lens 86, at the focal plane of the lens 84. Similarly, lenses 88 and 90 also form an afocal image system with the possible trial lens 86 at the focal plane of the lens 88 and the lens combination at the image plane at the focal plane of the lens 90. The focal plane of the lens 90 is located at the plate 44 of the wavefront sensor 42, earlier described with reference to FIG. 5. In a preferred embodiment, Lens 4 has a diameter of 30 mm and a focal length of 80 mm. Lens 5 has a diameter of 40 mm and a focal length of 120 mm. With the apparatus 10, measured wavefront slopes leaving the eye 14 are re-created at the aperture plane 44 and magnified by a factor of 1.5. Magnification of the wavefront 40 at the detector plane 54 reduces the wavefront slopes by the same degree. This extends the dynamic range of eye aberrations over which the device can measure.

By way of further explanation about the trial lens location or plane 86, because the wavefront 40 leaving the eye 14 is re-created at this location 86 with unity magnification, a trial lens of known refractive power inserted at this point should exactly compensate for a prescribed refractive error. For example, a perfect five-diopter spherical lens placed at this location should remove five diopters of spherical curvature from an incident wavefront, without altering other aberrations that may exist in the wavefront. The capability of inserting trial lenses at this location 86 extends the dynamic measurement range of the apparatus 10, without affecting wavefront analyzing capability.

In a preferred embodiment, and with reference again to FIG. 5, the aperture array 46 of the wavefront sensor 42 samples the incident wavefront 40, which forms focus spots 62 on the detector plane 54. This is repeated at the detector plane 54 for each aperture within the array 46. As a result, a localized direction of the wavefront 40 is determined for each of a plurality of wavelets 50 within the array. By way of example, the use of lenslets 92 (as an alternate embodiment of apertures 46 alone), with a focal length of 87 mm and a dimension of 0.768 mm, forms an aerial image of the retinal light source (the spot 16 described earlier with reference to FIG. 2) on the detector plane 54. If a plane wave, corresponding to an aberration-free eye, were measured, the lenslet 92 array would produce a regular array of focused spots on the image sensor. When the real eye 14 is measured, the wave aberration in the eye will displace the focus spot 62 (FIG. 5), of each lenslet 92 from the reference position 60 to the measured position 50 in proportion to the local slopes of the wavefront 40. The wavefront sensor 42 measures the local wavefront slopes at an array of sampling locations across the pupil 72, from which the wavefront 40 itself can be reconstructed.

As illustrated again with reference to FIG. 1, in an alternate embodiment of the present inventive methods, a fixation target 94 may be used to ensure that the patient is looking along the optical axis of the apparatus 10. The patient is asked to fixate on the target 94 located at the focal plane of a lens 96. By linearly moving the optics combination 96 of the fixation target 94, it is possible to provide the eye's spherical correction, and hence to make the fixation target 94 clearly visible to the subject. In one preferred use, the image of the fixation target 94 is intentionally undercorrected for each patient to ensure that the measured eye 14 is focused at infinity. By way of example, the fixation target consists of a dark cross-hair and a number of concentric circles on a white background that is back-illuminated by a tungsten lamp. The patient is asked to look at the center of the cross-hair. The position of the eye 14 in reference to the optical axis is recorded by CCD camera 98. This CCD camera 98 is conjugate, in effect coupled, to the eye's pupil 72 through a second lens combination 100, preferably mounted on the camera, and the lenses 82,84. In one method of the present invention, the camera 98 is used to view the eye 14 for aligning the eye within the path of the beam 12 for assuring that the beam passes through the pupil 72. The camera 98 is also useful in an alternate embodiment of the present invention, for viewing the size of the spot 16 formed on the retina 18 as the user changes the focus point 78 through various anterior surface locations in obtaining an optimum size of the spot 16.

By way of further example of effective uses of the present invention, the earlier described Zernike coefficients of an eye, taken collectively, can be used as discriminating as fingerprints or DNA. The Zernike coefficients for a person might be used for identification of that person for permitting access to a confidential area, allowing funds to be distributed through an ATM, and the like. Further, the present invention allows eye measurements for a passive subject, such as in the examination of a corpse or sedated animal. The present invention is operable with human eyes, as herein described, as well as those of an animal, bird, or fish eyes, and in particular, nonbiological focusing optical systems such as those found in cameras. The present invention is useful in developing optimized aspheric systems, where an aspheric element need to be designed last by observing and producing a single custom aspheric element that corrects the system. By way of example, the aspheric system may be designed on paper except for the correcting element, which would be developed experimentally using the present invention as herein described. The design of afocal systems such as a telescope, a searchlight, or a projector which require an added corrective focus element will benefit from the present invention.

Many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that modifications and alternate embodiments are intended to be included within the scope of the appended claims.

That which is claimed is:

1. A method for measuring vision defects of an eye comprising the steps of:
   focusing an optical beam behind a retina of the eye, for placing a finite source of secondary radiation on the retina, which secondary radiation is emitted from the retina as a reflected wavefront of radiation that passes through the eye;
   projecting the reflected wavefront onto a wavefront analyzer; and
   measuring distortions associated with the reflected wavefront.

2. The method recited in claim 1, wherein the optical beam comprises a collimated laser beam.

3. The method recited in claim 1, further comprising the steps of:
   generating a linearly polarized, collimated beam of light; and
   positioning a long-focal-length lens for directing the collimated beam of light through the long-focal-length lens, and wherein the focusing step includes the step of converging the collimated light through a small angle to a focal point behind the retina.

4. The method recited in claim 3, wherein the long-focal-length lens has a focal length in a range of approximately 0.5 to 5.0 meters.

5. The method recited in claim 3, further comprising the step controlling an amount of optical beam energy delivered to the eye.

6. The method recited in claim 1, wherein the distortion measuring step comprises the step of comparing the reflected wavefront received by the wavefront analyzer to a desirable wavefront received by the wavefront analyzer.

7. The method recited in claim 1, wherein the distortion measuring step comprises the step of determining an optical path difference between a plane wave and the wavefront emanating from the retina of the eye.

8. The method recited in claim 7, wherein the optical path difference results from a Zernike reconstruction of the wavefront.

9. The method recited in claim 1, wherein the distortion measuring step comprises the steps of:
   positioning an opaque plate having an aperture therein for transmitting a portion of the emitted wavefront therethrough;
   placing a light-sensitive material downstream of and in spaced relation to the opaque plate for receiving the portion of the reflected wavefront projected as a finite image onto a first position of the light-sensitive material;

projecting the reflected wavefront onto the plate for placing a first finite image onto the light-sensitive material;

projecting a desirable wavefront onto the plate for placing a second finite image at a second location on the light-sensitive material; and measuring a difference between the first position and the second position.

10. The method recited in claim 9, wherein the aperture comprises an aperture array and wherein the light-sensitive material comprises a CCD array.

11. The method recited in claim 10, wherein the aperture array comprises a lens carried within each aperture for focusing light passing through the aperture onto the CCD array.

12. The method recited in claim 1, further comprising the step of converting the measured distortions to an optical correction based on a deviation of the reflected wavefront from a desirable wavefront.

13. The method recited in claim 12, wherein the desirable wavefront comprises a planar wavefront.

14. The method recited in claim 13, wherein the polarizing step comprises the steps of:

providing a beamsplitter;

passing the reflected wavefront having an S-component and a P-component of polarization through the beamsplitter; and splitting the reflected wavefront by directing the P-component to the wavefront analyzer and the S-component therefrom.

15. The method recited in claim 1, further comprising the step of polarizing the optical beam.

16. The method recited in claim 1, further comprising the steps of:

positioning a fixation target for viewing;

focusing the eye on the fixation target for assuring that a patient whose eye is being measured is looking along a preferred direction.

17. The method recited in claim 16, further comprising the step of adjusting the fixation target for ensuring that the measured eye is focused at infinity.

18. The method recited in claim 1, further comprising the steps of:

viewing the pupil of the eye through a camera focused on the eye; and aligning the center of the eye along a beam path of the optical beam for confirming passage of the beam through the pupil of the eye.

19. A method for measuring vision characteristics of an eye, the method comprising the steps of:

projecting an optical beam through a sufficiently small angle about an optical path for passing the beam through the pupil of the eye and providing a finite spot on the retina of the eye;

focusing the optical beam proximate behind a retina of the eye for placing a finite source of secondary radiation on the retina, which secondary radiation provides light emitted from the retina and through the pupil as a reflected wavefront of radiation; and directing the reflected wavefront onto a wavefront analyzer for measuring distortions associated with the reflected wavefront.

20. The method recited in claim 19, wherein the optical beam comprises a laser beam.

21. The method recited in claim 19, further comprising the steps of:

generating a linearly polarized optical beam; and positioning a long-focal-length lens for directing the optical beam therethrough, and wherein the focusing step includes the step of directing the optical beam through the long-focal-length lens for providing the small angle in which to focus the optical beam.

22. The method recited in claim 21, wherein the long-focal-length lens has a focal length of at least one-half meter in length.

23. The method recited in claim 19, further comprising the steps of:

providing a shutter within a beam path of the optical beam; and controlling an amount of optical beam energy delivered to the eye by operating the shutter from a closed position to an open position.

24. The method recited in claim 19, further comprising the step of measuring an optical path difference between a desirable wavefront and the wavefront emanating from the retina of the eye.

25. The method recited in claim 24, wherein the measuring step comprises the steps of:

positioning an opaque plate having an aperture array therein for transmitting a plurality of emitted wavelets of the emitted wavefront therethrough; and receiving finite images of the plurality of emitted wavelets on a light-sensitive material downstream of and in spaced relation to the opaque plate.

26. The method recited in claim 25, further comprising the steps of:

determining positions for each of the plurality of emitted wavelet finite images;

projecting the desirable wavefront onto the plate for placing a plurality of reference wavelets onto the light-sensitive material;

determining positions for each of the plurality of reference wavelet finite images; and measuring a displacement between finite images, respectively, for the emitted wavelets and reference wavelets.

27. The method recited in claim 26, further comprising the step of converting the displacement to an optical correction based on a difference between the reflected wavefront and the desirable wavefront.

28. The method recited in claim 27, wherein the desirable wavefront comprises a planar wavefront.

29. The method recited in claim 28, further comprising the steps of:

polarizing the optical beam;

passing the reflected wavefront through a beam splitter, wherein an S-component and a P-component of the polarized optical beam pass through the beamsplitter; and splitting the reflected wavefront by directing the P-component to the wavefront analyzer and the S-component therefrom.

30. A method for measuring vision characteristics of an eye comprising focusing an optical beam behind a retina of the eye for providing a finite source of secondary radiation on the retina of the eye, which secondary radiation is emitted from the retina as a reflected wavefront of radiation that passes through the eye.

31. The method recited in claim 30, further comprising projecting the reflected wavefront onto a wavefront analyzer and measuring differences between the reflected wavefront and a desirable wavefront.

32. The method recited in claim 30, further comprising generating a linearly polarized, collimated beam of light and positioning a long-focal-length lens for directing the collimated beam of light through the long-focal-length lens, wherein the focusing includes converging the collimated light through a small angle to a focal point on the anterior surface of the eye.

33. The method recited in claim 32, wherein the linearly polarized collimated beam comprises a laser beam.

34. The method recited in claim 30, further comprising viewing the size of the finite secondary radiation source on the retina, and varying focus locations behind the retina for selecting a desired size of the source.

35. A method for measuring optical characteristics of an optical system, the method comprising the steps of:

focusing an optical beam proximate a posterior surface of the optical system for placing a finite source of secondary radiation on a focal surface of the optical system, wherein the posterior surface is other than the focal surface, which secondary radiation is emitted from the focal surface as a reflected wavefront of radiation that passes through the optical system;

projecting the reflected wavefront onto a wavefront analyzer; and measuring characteristics of the optical system associated with the reflected wavefront.

36. A method for measuring vision defects of an eye comprising the steps of:

focusing an optical beam anterior of the retina of the eye, but not on the retina, for placing a finite source of secondary radiation on the retina, which secondary radiation is emitted from the retina as a reflected wavefront of radiation that passes through the eye;

projecting the reflected wavefront onto a wavefront analyzer; and measuring distortions associated with the reflected wavefront.

* * * * *